(12) United States Patent
Papaioannou et al.

(10) Patent No.: US 10,925,668 B2
(45) Date of Patent: *Feb. 23, 2021

(54) CATHETER WITH IRRIGATED TIP ELECTRODE WITH POROUS SUBSTRATE AND HIGH DENSITY SURFACE MICRO-ELECTRODES

(71) Applicant: Biosense Webster (Israel) Ltd., Yokneam (IL)

(72) Inventors: Athanassios Papaioannou, Los Angeles, CA (US); Christopher Thomas Beeckler, Brea, CA (US); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/551,300

(22) Filed: Aug. 26, 2019

(65) Prior Publication Data

US 2019/0380775 A1    Dec. 19, 2019

Related U.S. Application Data

(63) Continuation of application No. 16/049,737, filed on Jul. 30, 2018, now Pat. No. 10,390,880, which is a
(Continued)

(51) Int. Cl.
*A61B 18/14*    (2006.01)
*A61B 5/042*    (2006.01)
(Continued)

(52) U.S. Cl.
CPC ........ *A61B 18/1492* (2013.01); *A61B 5/0422* (2013.01); *A61B 5/6852* (2013.01);
(Continued)

(58) Field of Classification Search
CPC .......................... A61B 5/0422; A61B 18/1492
See application file for complete search history.

(56) References Cited

U.S. PATENT DOCUMENTS 3,855,638 A    12/1974    Pilliar
3,890,977 A    6/1975    Wilson
(Continued)

FOREIGN PATENT DOCUMENTS

CN    203122582    8/2013
EP    0123456 A2    10/1984
(Continued)

OTHER PUBLICATIONS

European Search Report for EP Application No. 15202353.7, dated Jun. 8, 2016, 7 pages.
(Continued)

*Primary Examiner* — Lee S Cohen
(74) *Attorney, Agent, or Firm* — Lewis Roca Rothgerber Christie LLP

(57) ABSTRACT

A catheter has a multifunctional "virtual" tip electrode with a porous substrate and a multitude of surface microelectrodes. The surface microelectrodes are in close proximity to each other and in a variety of configurations so as to sense tissue for highly localized intracardiac signal detection, and high density local electrograms and mapping. The porous substrate allows for flow of conductive fluid for ablating tissue. The surface microelectrodes can be formed via a metallization process that allows for any shape or size and close proximity, and the fluid "weeping" from the porous substrate provides more uniform irrigation in the form of a thin layer of saline. The delivery of RF power to the catheter tip is based on the principle of "virtual electrode," where the conductive saline flowing through the porous tip acts as the electrical connection between the tip electrode and the heart surface. The substrate and the surface electrodes are con-
(Continued)

structed of MRI compatible materials so that the physician can conduct lesion assessment in real time during an ablation procedure. The surface electrodes include noble metals, including, for example, platinum, gold and combinations thereof.

20 Claims, 13 Drawing Sheets

Related U.S. Application Data continuation of application No. 14/586,907, filed on Dec. 30, 2014, now Pat. No. 10,034,707.

(51) Int. Cl.
*A61B 5/00* (2006.01)
*A61B 18/00* (2006.01)

(52) U.S. Cl.
CPC ........... *A61B 2018/00029* (2013.01); *A61B 2018/00065* (2013.01); *A61B 2018/00148* (2013.01); *A61B 2018/00577* (2013.01); *A61B 2018/00642* (2013.01); *A61B 2018/00702* (2013.01); *A61B 2018/00791* (2013.01); *A61B 2018/00839* (2013.01); *A61B 2018/1467* (2013.01); *A61B 2018/1472* (2013.01); *A61B 2018/1497* (2013.01); *A61B 2218/002* (2013.01)

(56) References Cited

U.S. PATENT DOCUMENTS

| | | | |
|---|---|---|---|
| 4,101,984 A | 7/1978 | MacGregor |
| 4,167,607 A | 9/1979 | de Nora et al. |
| 4,506,680 A | 3/1985 | Stokes |
| 4,547,094 A | 10/1985 | Kennedy et al. |
| 4,574,094 A | 3/1986 | DeLuca et al. |
| 4,819,662 A | 4/1989 | Heil, Jr. et al. |
| 4,844,099 A | 7/1989 | Skalsky et al. |
| 4,934,381 A | 6/1990 | MacGregor |
| 4,984,581 A | 1/1991 | Stice |
| 5,096,749 A | 3/1992 | Harada et al. |
| 5,209,734 A | 5/1993 | Hurley et al. |
| 5,269,752 A | 12/1993 | Bennett |
| 5,357,979 A | 10/1994 | Imran |
| 5,383,923 A | 1/1995 | Webster, Jr. |
| 5,391,199 A | 2/1995 | Ben-Haim |
| 5,443,489 A | 8/1995 | Ben-Haim |
| 5,462,521 A | 10/1995 | Brucker et al. |
| 5,522,815 A | 6/1996 | Durgin, Jr. et al. |
| 5,546,951 A | 8/1996 | Ben-Haim |
| 5,558,091 A | 9/1996 | Acker et al. |
| 5,568,809 A | 10/1996 | Ben-Haim |
| 5,643,197 A | 7/1997 | Brucker et al. |
| 5,681,344 A | 10/1997 | Kelly |
| 5,688,267 A | 11/1997 | Panescu et al. |
| 5,690,805 A | 11/1997 | Thorn et al. |
| 5,725,938 A | 3/1998 | Jin et al. |
| 5,797,903 A | 8/1998 | Swanson et al. |
| 5,843,076 A | 12/1998 | Webster, Jr. et al. |
| 5,846,238 A | 12/1998 | Jackson et al. |
| 5,868,736 A | 2/1999 | Swanson et al. |
| 5,910,129 A | 6/1999 | Koblish et al. |
| 5,913,856 A | 6/1999 | Chia et al. |
| 5,964,757 A | 10/1999 | Ponzi |
| 6,017,338 A | 1/2000 | Brucker et al. |
| 6,032,077 A | 2/2000 | Pomeranz |
| 6,120,476 A | 9/2000 | Fung et al. |
| 6,123,699 A | 9/2000 | Webster, Jr. |
| 6,171,275 B1 | 1/2001 | Webster, Jr. |
| 6,241,666 B1 | 6/2001 | Pomeranz et al. |
| 6,405,078 B1 | 6/2002 | Moaddeb et al. |
| 6,458,123 B1 | 10/2002 | Brucker et al. |
| 6,458,127 B1 | 10/2002 | Truckai et al. |
| 6,466,818 B1 | 10/2002 | Moaddeb et al. |
| 6,475,213 B1 | 11/2002 | Whayne et al. |
| 6,611,699 B2 | 8/2003 | Messing |
| 6,669,692 B1 | 12/2003 | Nelson et al. |
| 6,893,437 B2 | 5/2005 | Swanson et al. |
| 7,066,935 B2 | 6/2006 | Swoyer et al. |
| 7,104,989 B2 | 9/2006 | Skarda |
| 7,311,708 B2 | 12/2007 | McClurken |
| 7,537,595 B2 | 5/2009 | McClurken |
| 7,623,899 B2 | 11/2009 | Worley et al. |
| 7,857,809 B2 | 12/2010 | Drysen |
| 7,959,628 B2 | 6/2011 | Schaer et al. |
| 8,262,653 B2 | 9/2012 | Plaza |
| 8,623,010 B2 | 1/2014 | Ocel et al. |
| 9,370,329 B2 | 6/2016 | Tun et al. |
| 10,390,880 B2 * | 8/2019 | Papaioannou ....... A61B 5/0422 |
| 2004/0092806 A1 | 5/2004 | Sagon et al. |
| 2008/0097429 A1 | 4/2008 | McClurken |
| 2008/0243214 A1 | 10/2008 | Koblish |
| 2013/0060245 A1 | 3/2013 | Grunewald et al. |
| 2014/0058376 A1 | 2/2014 | Horn et al. |

FOREIGN PATENT DOCUMENTS

| | | |
|---|---|---|
| EP | 1803411 A2 | 7/2007 |
| JP | 4361136 B2 | 8/2009 |
| JP | 201352241 A | 3/2013 |
| WO | 9502995 A1 | 2/1995 |
| WO | WO 9745156 A2 | 12/1997 |

OTHER PUBLICATIONS

Extended European Search Report dated Jul. 7, 2017, issued in corresponding EP Application No. 17153207.0, 7 pages.
English translation of CN Office action dated Jul. 17, 2019, issued in CN Application No. 201511009217.X, 16 pages.
English translation of JP Office action dated Oct. 29, 2019, issued in JP Application No. 2015-255846, 4 pages.

* cited by examiner

CATHETER WITH IRRIGATED TIP ELECTRODE WITH POROUS SUBSTRATE AND HIGH DENSITY SURFACE MICRO-ELECTRODES

CROSS-REFERENCE TO RELATED APPLICATION(S)

This application is a continuation of and claims priority to and the benefit of U.S. application Ser. No. 16/049,737 filed Jul. 30, 2018, now U.S. Pat. No. 10,390,880, which claims priority to and the benefit of U.S. application Ser. No. 14/586,907, filed Dec. 30, 2014, now U.S. Pat. No. 10,034,707, the entire contents of both of which are incorporated herein by reference.

FIELD OF INVENTION

This invention relates to catheters and electrophysiologic catheters, in particular, catheters for cardiac tissue ablation and diagnostics.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in various tissue regions in or near the heart, for example, the ventricles, the atria and/or and adjacent structures such as areas of the pulmonary veins. Regardless of the sources, unwanted signals are conducted abnormally through heart tissue where they can initiate and/or maintain arrhythmia.

Procedures for treating arrhythmia include surgically disrupting the origin of the signals causing the arrhythmia, as well as disrupting the conducting pathways for such signals. More recently, it has been found that by mapping the electrical properties of the heart muscle in conjunction with the heart anatomy, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

A typical ablation procedure involves the insertion of a catheter having a tip electrode at its distal end into a heart chamber. A reference electrode is provided, generally taped to the patient's skin. Radio frequency (RF) current is applied to the tip electrode, and flows through the surrounding media, i.e., blood and tissue, toward the reference electrode. The distribution of current depends on the amount of electrode surface in contact with the tissue, as compared to blood which has a higher conductivity than the tissue. Heating of the tissue occurs due to its electrical resistivity. If the tissue is heated sufficiently, cellular and other protein destruction ensues; this in turn forms a lesion within the heart muscle which is electrically non-conductive. During this process, heating of the electrode also occurs as a result of conduction from the heated tissue to the electrode itself. If the electrode temperature becomes sufficiently high, possibly above 50 degree C., blood clot could form on the surface of the electrode. If the temperature continues to rise, more blood clot is formed while dehydration ensues.

The tip temperature increase and the associated clot formation have two consequences: increased electrical impedance and increased probability for stroke. The former relates to clot dehydration. Because dehydrated biological material has a higher electrical resistance than heart tissue, impedance to the flow of electrical energy into the tissue also increases. Increased impedance leads to sub-optimal energy delivery to the tissue which results in inadequate lesion formation, reduced ablation efficiency and eventually to sub-optimal clinical outcome. The latter, a safety hazard, is due to possible dislodgment of the formed clot and relocation in the brain vasculature. It is therefore beneficial from a safety perspective as well as ablation efficiency to minimize the tip temperature increase and clot formation. This should be accomplished without compromising the formation of lesions of appropriate sizes.

In a typical application of RF current to the endocardium, circulating blood provides some cooling of the ablation electrode. However, there is typically a stagnant area between the electrode and tissue which is susceptible to the formation of dehydrated proteins and coagulum. As power and/or ablation time increases, the likelihood of an impedance rise also increases. As a result of this process, there has been a natural upper bound on the amount of energy which can be delivered to cardiac tissue and therefore the size of RF lesions. In clinical practice, it is desirable to reduce or eliminate impedance rises and, for certain cardiac arrhythmias, to create larger lesions. One method for accomplishing this is to monitor the temperature of the ablation electrode and to control the RF current delivered to the ablation electrode based on this temperature. If the temperature rises above a pre-selected value, the current is reduced until the temperature drops below this value. This method has reduced the number of impedance rises during cardiac ablations but has not significantly increased lesion dimensions. The results are not significantly different because this method continues to rely on the cooling effect of the blood which is dependent on the location within the heart and the orientation of the catheter to the endocardial surface.

Another method is to irrigate the ablation electrode, e.g., with physiologic saline at room temperature, to actively cool the ablation electrode instead of relying on the more passive physiological cooling provided by the blood. Additionally, due to the irrigation-mediated dilution of blood around the tip, the probability for clot creation is further reduced. Thus, irrigation tip cooling and blood dilution allow for safer increase of applied RF power. This results in lesions which tend to be larger usually measuring about 10 to 12 mm in depth.

The clinical effectiveness of irrigating the ablation electrode is dependent upon the distribution of flow within and around the surface of the tip electrode structure as well as the rate of irrigation flow through the tip. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. Irrigation is utilized during the entire time the catheter resides inside the patient's body. Higher flow rate is used during ablation while lower-maintenance-flow rate is required in order to prevent back flow of blood into the coolant passages during non-ablation time. The coolant flow rate must be balanced against the amount of fluid that can be safely injected into the patient.

Thus, reducing coolant flow by utilizing it as efficiently as possible is a desirable design objective.

One method for designing an ablation electrode which efficiently utilizes coolant flow is the use of a porous material structure. Such designs have the advantage of distributing the coolant evenly across the entire electrode structure. This balanced cooling results in a) eradication of possible surface or interior hot spots, and b) uniform dilution of blood at the vicinity of the electrode, thus further minimizing the chance for clot formation. Such designs are described in U.S. Pat. Nos. 6,405,078 and 6,466,818 to Moaddeb et al., the entire disclosures of which are incorporated herein by reference. Moaddeb describes the use of sintered metal particles to create a porous tip electrode. In addition, Moaddeb uses a non-conductive insert implanted into the porous tip electrode for mounting a thermocouple, lead wire and/or irrigation tube within the porous tip electrode. However, during irrigation the sintered metal particles can disintegrate and break away from the electrode structure. This-undesirable-particle dislodgement may be further facilitated during ablation. Additionally, (and in the context of our MRI compatibility claims-see below) the metallic material proposed for such porous tip is not optimal for MRI imaging. Furthermore, the proposed tip does not allow for high density mapping—a highly desired feature for accurate arrhythmia diagnosis. Consequently, a desire arises for a porous electrode having increased structural integrity, being compatible with the MRI environment, and allowing for high mapping density.

A porous tip electrode catheter is also described in U.S. Pat. No. 8,262,653 to Plaza. The porous tip electrode comprises a porous material through which fluid can pass. The porous tip electrode is covered with a thin coating of conductive metal having openings (pores) through which fluids can pass. However, the porosity of such thin conductive coating is not easily controlled leading to inconsistent pore size and distribution. Therefore, distribution of irrigation fluid around the tip electrode may not be even or uniform. Furthermore, in this design, RF power delivery is achieved via direct connection (e.g. by soldering or other similar technique) of the RF power line to the tip's outer conductive coat. Thus, the presence of the generally non-uniform porous coating is necessary in order to establish electrical contact of the tip to the heart tissue.

Safe and efficacious ablation depends not only on optimal irrigation arrangement for the tip but also on accurate mapping of the electrophysiological behavior of the heart, which would allow for accurate diagnosis and appropriate tissue targeting. The greater the accuracy of the mapping the more accurate the diagnosis and thus the effectiveness of treatment. Improved (high resolution) cardiac mapping requires the use of a multitude of electrodes in close proximity to sense electrical activity within a small area, for example, a square centimeter or less.

Metallization of ceramics is a well-established technique and is widely used in a multitude of electronics and engineering disciplines, including fabrication of RF electronic circuits. Metallization involves the application of metal on ceramic substrates, including the formation of conductive regions, such as metallized conductor patterns or uniform metal layers on surfaces of ceramic substrates. Common ceramic substrates include aluminum oxide, beryllium oxide, ferrite, barium titanate, as well as quartz or borosilicate. Generally, ceramic metallization processes fall into three categories: thin-film, thick-film, and co-firing techniques. In the thin film approach, a thin layer of metal is deposited by vacuum processes such as sputtering, evaporation, chemical vapor deposition, and laser ablation. Electroless and electrolytic plating are also frequently grouped in the thin film category. To enhance adhesion, a preliminary adhesion-promoting layer, such as chromium or titanium, is often deposited. Thick film methods involve printing metal pastes, typically metal powders mixed with glass frits and organic binders onto ceramic substrates. The printed substrates are fired to form conductive paths on the ceramic. In the co-firing approach, unfired "green" ceramic surfaces are coated with patterned metal paste lines. The printed green ceramic is fired both to sinter the material and form the conductive metal patterns. Metallization processes are described, for example, in U.S. Pat. No. 4,547,094 to DeLuca, et al.; U.S. Pat. No. 5,096,749 to Harada, et al.; U.S. Pat. No. 5,690,805 to Thorn, et al.; and U.S. Pat. No. 5,725,938 Jin, et al. Metallization depending on the type of metallization process and the substrate may include gold, platinum, or other biocompatible metals suitable for intracardial signal acquisitions.

While ablation has revolutionized the treatment of cardiac arrhythmias, ablation can be improved where physicians can assess lesions in real time. The use of magnetic resonance imaging (MRI) during an ablation procedure could enable physicians to assess lesions in real time. However, the ablation catheter and other associated accessory equipment can interfere with the imaging process, causing local distortions in the MRI scans. Use of appropriate MRI compatible materials is necessary to minimize these image distortions. Safety experts have cleared some metals for use during MRIs, including titanium, cobalt-chromium, copper, selected stainless steel alloys. Non-ferromagnetic metals are also MRI compatible. Such materials include copper, brass, silver, gold, aluminum, lead, magnesium, platinum and tungsten. Ceramic materials as well as other thermoplastic polymers are non-metallic and as such are highly desirable as MRI compatible materials. They not only present minimal image distortion but being electrical insulators they present no heating effects due to absence of internally induced electrical currents. Ceramic materials of porous construction are proposed in the current invention as materials for the construction of the catheter's tip.

In view of the foregoing, it is desirable to provide a catheter with a dome tip electrode made of a porous substrate for more uniform irrigation, where the dome tip electrode incorporates surface electrodes made via a metallization, printing or other process for any desirable surface electrode pattern that provides multiple electrodes in close proximity for high density mapping. It is also desirable to provide a catheter where the substrate and the surface electrodes are MRI compatible so that the physician can conduct lesion assessment in real time during an ablation procedure.

SUMMARY OF THE INVENTION

The present invention is directed to a catheter having a multifunctional "virtual" tip electrode with a porous substrate and a multitude of surface microelectrodes. The surface microelectrodes in close proximity to each other and in a variety of configurations sense tissue for highly localized intracardiac signal detection, and high density local electrograms and mapping and the porous substrate allows for flow of conductive fluid for ablating tissue. The surface microelectrodes can be formed via a metallization process that allows for any shape or size and close proximity, and the fluid "weeping" from the porous substrate provides more uniform irrigation in the form of a thin layer of saline. The delivery of RF power to the catheter tip is based on the principle of "virtual electrode," where the conductive saline flowing through the porous tip acts as the electrical connection between the tip electrode and the heart surface.

Moreover, the substrate and the surface electrodes are constructed of MRI compatible materials so that the physician can conduct lesion assessment in real time during an ablation procedure. The surface electrodes include noble metals, including, for example, platinum, gold and combinations thereof.

In some embodiments, the catheter includes an elongated catheter body, and a distal electrode member having a porous substrate and a plurality of distinct surface microelectrodes. A plurality of lead wires are connected to the surface microelectrodes for transmitting electrical signals sensed by the microelectrodes. The porous substrate has an interior chamber adapted to receive conductive fluid which is in electrical contact with a lead wire that extends into the chamber, wherein such electrified fluid passes from the chamber to outside the substrate for distal irrigation and tissue ablation.

In some detailed embodiments, the porous substrate is comprised of a ceramic material. The substrate has a plurality of surface microelectrodes ranging between about one and 20. Each surface microelectrode has a surface area ranging between 0.2 mm$^2$ and 2 mm$^2$.

In some detailed embodiments, the porous substrate and the chamber both have a generally cylindrical shape, with a generally uniform wall thickness between the chamber and the outer surface of the substrate.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
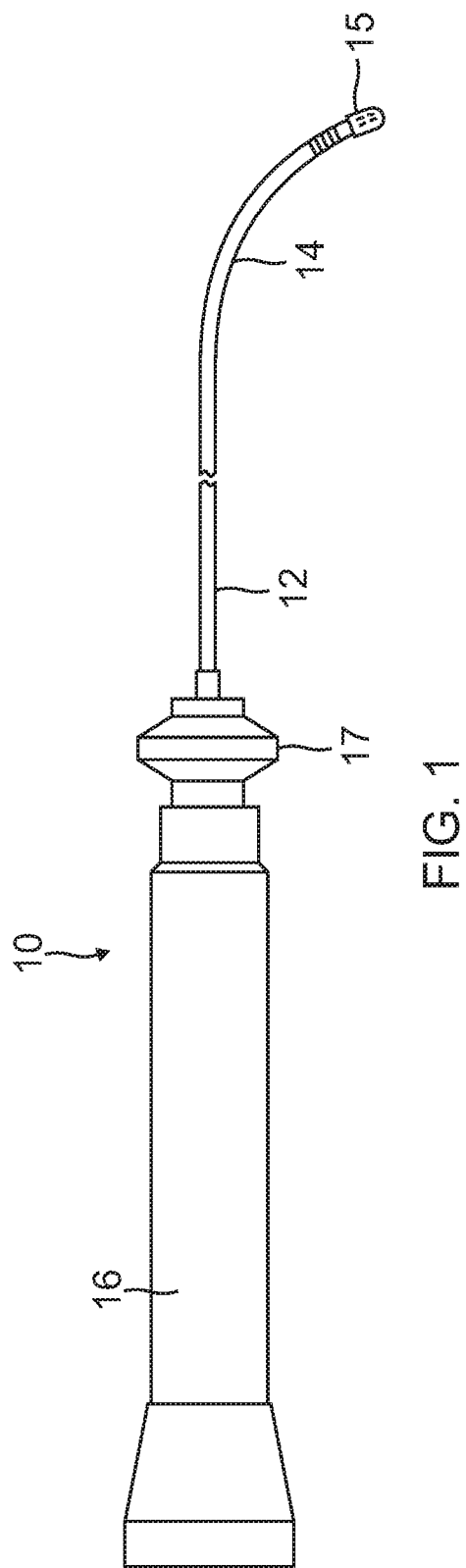
FIG. 1 is a perspective view of a catheter of the present invention, in accordance with one embodiment.

In one embodiment of the invention, there is provided a steerable catheter having an irrigated tip adapted for diagnostic and/or therapeutic procedures. As shown in FIG. 1, catheter 10 comprises an elongated catheter body 12 having proximal and distal ends, an intermediate deflection section 14 extending from a distal end of the catheter body 12, a tip electrode section 15 extending from a distal end of the catheter body 12, and a control handle 16 at the proximal end of the catheter body 12.

Figure 2A:
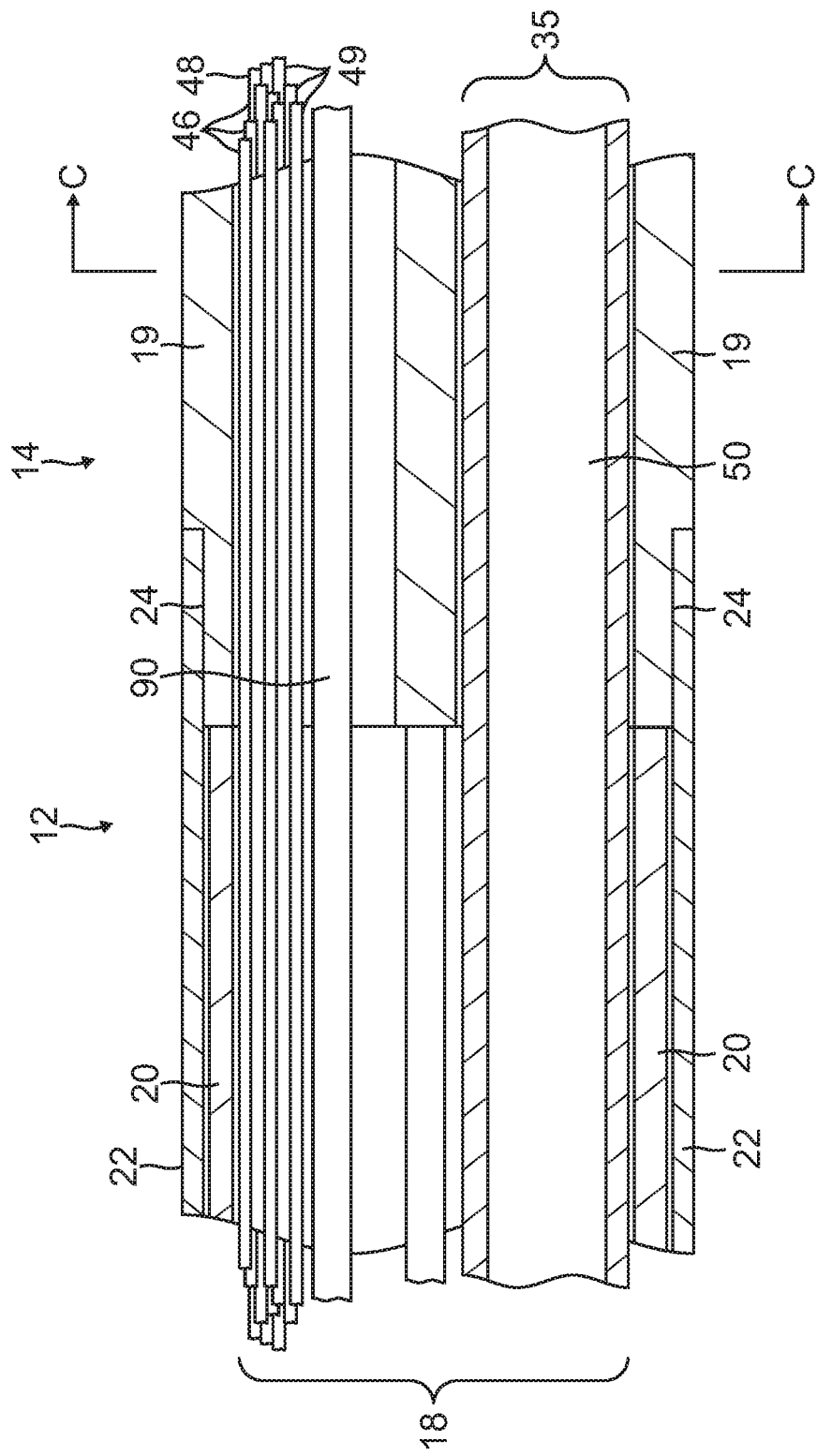
FIG. 2A is a side cross-sectional view of the catheter of FIG. 1, including a junction between a catheter body and a deflection section, taken along a first diameter.
Figure 2B:
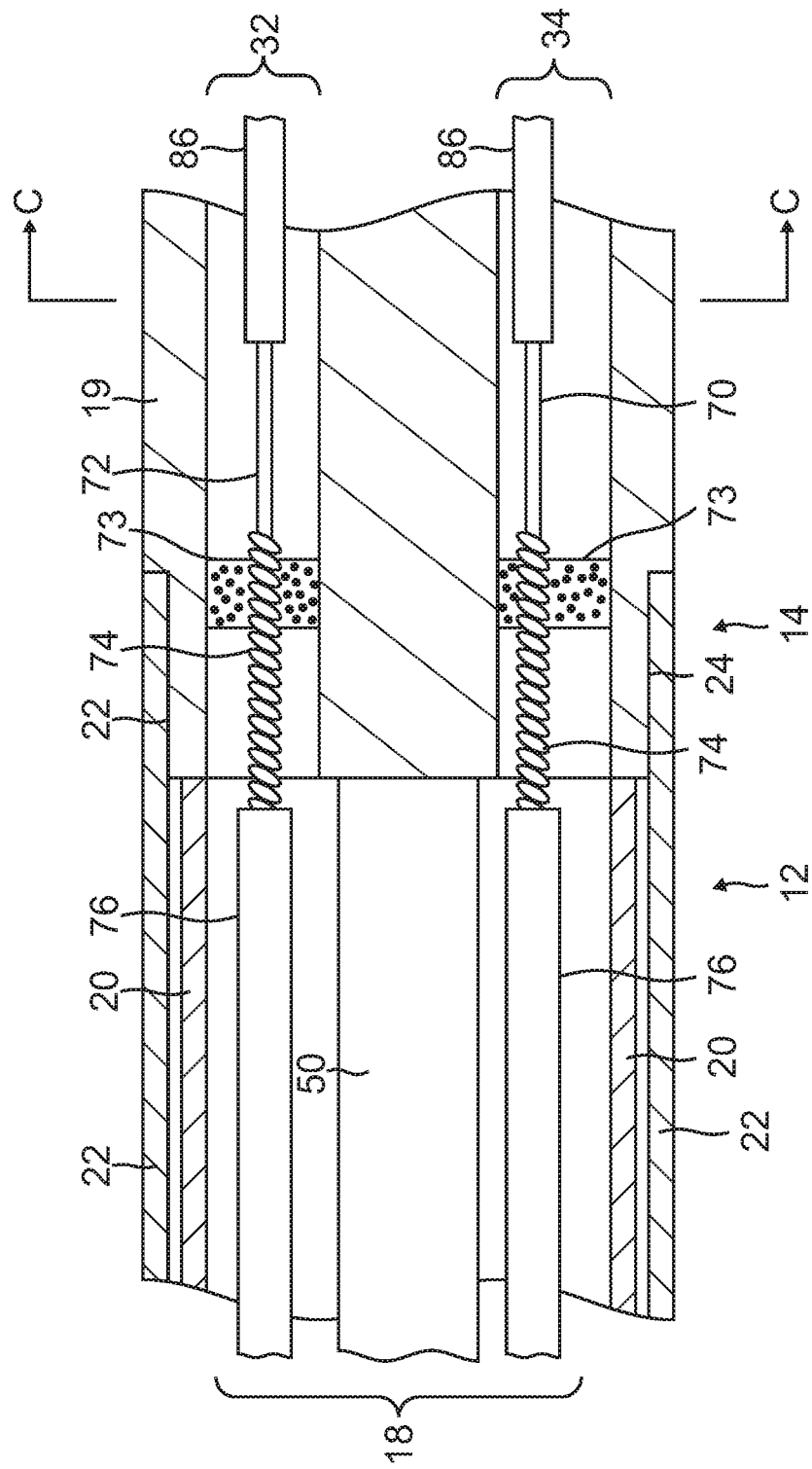
FIG. 2B is a side cross-sectional view of the catheter of FIG. 1, including the junction of FIG. 2A, taken along a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable but substantially non-compressible along its length. The catheter body 12 can be of any suitable construction and made of any suitable material. In one embodiment, the catheter body 12 comprises an outer wall 22 made of a polyurethane or PEBAX. The outer wall 22 comprises an imbedded braided mesh of high-strength steel, stainless steel or the like to increase torsional stiffness of the catheter body 12 so that, when the control handle 16 is rotated axially, the rest of the catheter, including the sections 14 and 16, also rotates axially. The outer diameter of the catheter body 12 is not critical, but is preferably no more than about 8 french, more preferably about 7 french, still more preferably about 5 french. Likewise, the thickness of the outer wall 22 is not critical, but is thin enough so that the central lumen 18 can accommodate an irrigation tube, puller wire(s), lead wires, and any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional and longitudinal stability. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness. A particularly preferred catheter has an outer wall 22 with an outer diameter of from about 0.090 inches to about 0.098 inches and an inner diameter of from about 0.061 inches to about 0.065 inches and a polyimide stiffening tube 20 having an outer diameter of from about 0.060 inches to about 0.064 inches and an inner diameter of from about 0.051 inches to about 0.056 inches.

Figure 2C:
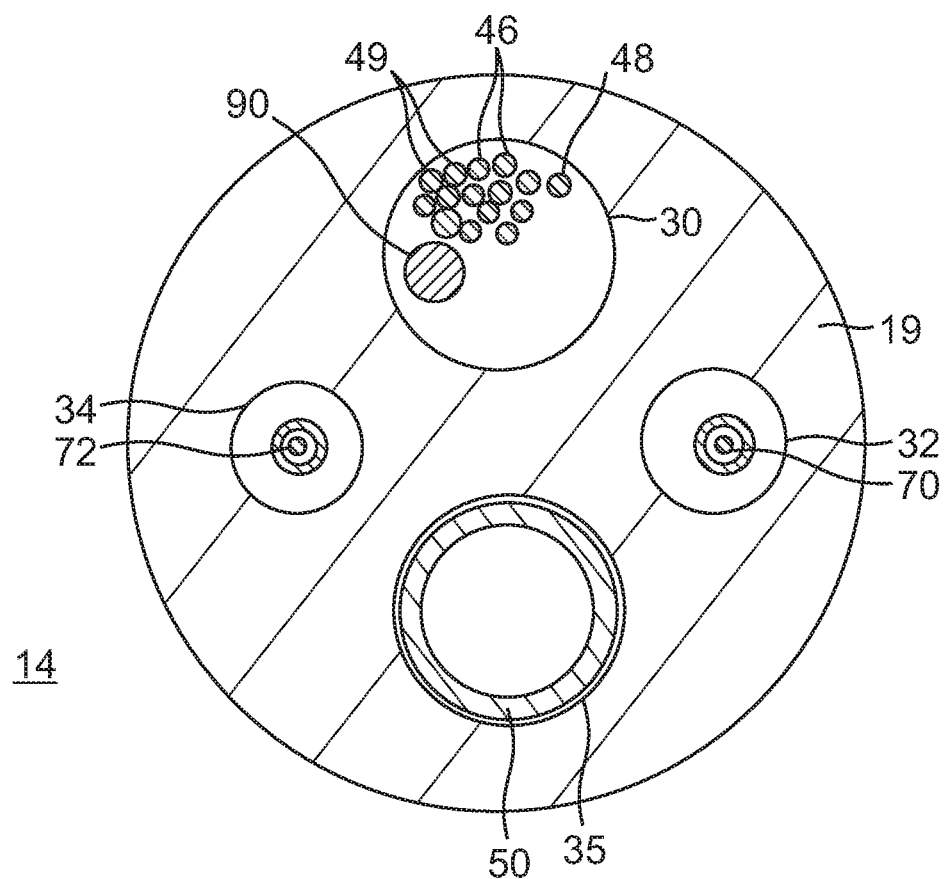
FIG. 2C is an end cross-sectional view of the deflection section of FIGS. 2A and 2B, taken along line C-C.

As shown in FIGS. 2A, 2B, and 2C, the intermediate deflectable section 14 comprises a short section of tubing 19 having multiple lumens, including off-axis lumens 30, 32, 34 and 35. The tubing 19 is made of a suitable non-toxic material that is preferably more flexible than the catheter body 12. In one embodiment, the material for the tubing 19 is braided polyurethane, i.e., polyurethane with an imbedded mesh of braided high-strength steel, stainless steel or the like. The outer diameter of the deflection section 14, like that of the catheter body 12, is preferably no greater than about 8 french, more preferably about 7 french, still more preferably about 5 french. The size of the lumens is not critical. In one embodiment, the deflection section 14 has an outer diameter of about 7 french (0.092 inches) and the second lumen 32 and third lumen 34 are generally about the same size, each having a diameter of from about 0.020 inches to about 0.024 inches, preferably about 0.022 inches, with the first and fourth lumens 30 and 35 having a slightly larger diameter of from about 0.032 inches to about 0.038 inches, preferably about 0.036 inches.

A means for attaching the catheter body 12 to the deflection section 14 is illustrated in FIGS. 2A and 2B. The proximal end of the deflection section 14 comprises an outer circumferential notch 24 that receives the inner surface of the outer wall 22 of the catheter body 12. The deflection section 14 and catheter body 12 are attached by adhesive (e.g. polyurethane glue) or the like. Before the deflection section 14 and catheter body 12 are attached, however, the stiffening tube 20 is inserted into the catheter body 12. The distal end of the stiffening tube 20 is fixedly attached near the distal end of the catheter body 12 by forming a glue joint (not shown) with polyurethane glue or the like. Preferably, a small distance, e.g., about 3 mm, is provided between the distal end of the catheter body 12 and the distal end of the stiffening tube 20 to permit room for the catheter body 12 to receive the notch 24 of the deflection section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter, a second glue joint (not shown) is formed between the proximal ends of the stiffening tube 20 and outer wall 22 using a slower drying but stronger glue, e.g. polyurethane.

At the distal end of the deflection section 14 is the distal tip electrode section 15 having a connector tube 27 and a tip electrode 36. In the illustrated embodiment of FIGS. 3A and 3B, the connector tube 27 is a relative short piece of tubing, about 1 cm in length, for example, made of polyetheretherketone (PEEK). The proximal end of the connector tube 27 has a circumferential notch whose outer surface is surrounded by an inner surface of a circumferential notch formed in the distal end of the tubing 10 of the deflection section 14. The ends are bonded to each other by polyurethane glue or the like.

Figure 4:
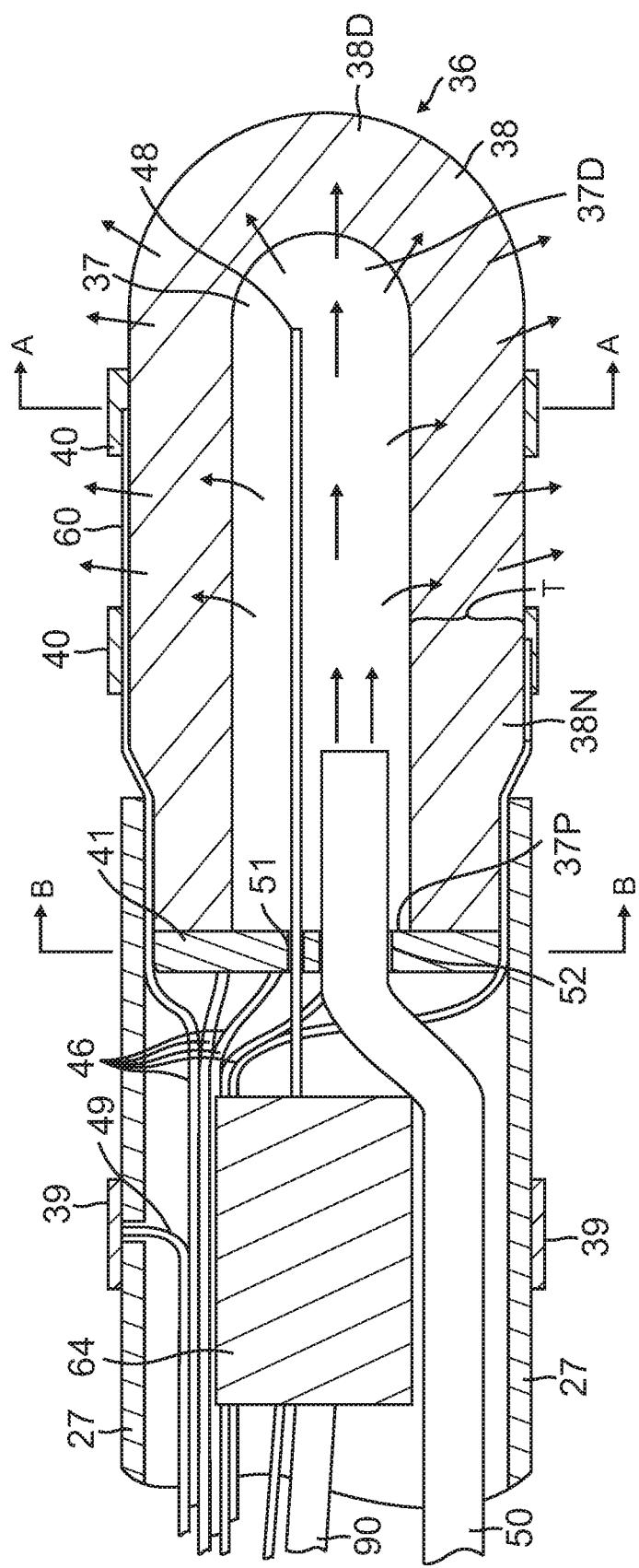
FIG. 4 is a side cross-sectional view of the catheter of FIG. 1, including a distal electrode section.
Figure 4A:
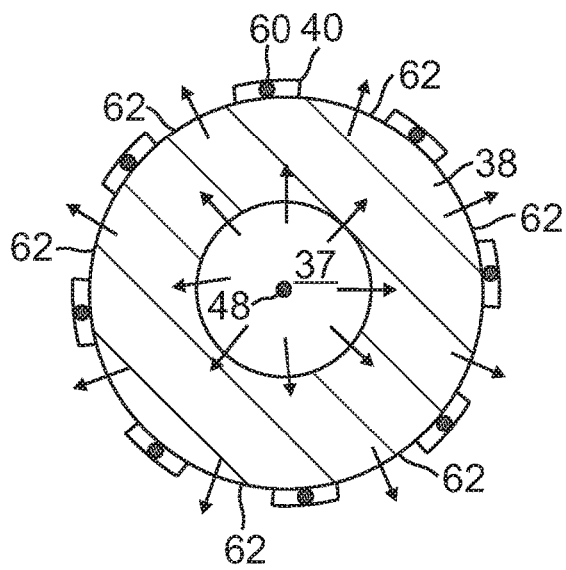
FIG. 4A is an end cross-sectional view of the distal electrode section of FIG. 4, taken along line A-A.

As shown in FIG. 4, the tip electrode 36 has a diameter about the same as the outer diameter of the tubing 19 and the connector tube 27. The tip electrode 36 includes a porous substrate 38 and a plurality of surface electrodes 40. The porous substrate 38 is formed by porous ceramic material or any other suitable non-conductive polymer, such as polyethylene, or polytetrafluoroethylene (e.g., Teflon®). In the illustrated embodiment, the substrate 38 has an elongated cylindrical shape with a narrower proximal stem portion 38N. The substrate 38 is formed with an interior chamber 37 that also has a similar elongated cylindrical shape extending longitudinally in the substrate 38. In one embodiment, the porous substrate 38 has a total length ranging from about 6 mm to about 9 mm, more preferably about 7 mm. For a 7 mm long tip electrode, each of the body form 38B and the proximal stem portion 38N may have a length of about 3.5 mm.

The chamber 37 has an opening 37P at the proximal end of the substrate 38 and a distal end 37D near the distal end of the substrate. It is understood that the chamber 37 and the substrate need not have the same general shape, and further that depending on the volume of the chamber 37 the thickness T of the wall between the chamber 37 and the outer surface of the substrate may be varied as desired or appropriate.

Abutting the proximal face of the substrate stem portion 38N, a plug member 41 seals the proximal face and plugs the opening thus enclosing the chamber 37. As shown in FIG. 4, the plug member 41 has a first through-hole 51 for lead wire 48 to pass through and enter into the chamber 37 and a second through-hole 52 for receiving a distal end of an irrigation tubing 50 which supplies fluid, e.g., saline or any electrically conductive fluid, into the chamber 37.

In the embodiment of FIG. 4, the proximal stem portion 38N is received in a distal end of the connector tube 27. The stem portion 38N and the connector tube 27 are attached by polyurethane glue or the like.

The porous non-conductive material of the substrate 38 can be made using any conventional technique In the illustrated embodiment, the non-conductive material comprises sintered ceramic powder, or polymer particles formed from polyethylene or Teflon. As used herein, the term "sinter" refers to the process of bonding adjacent particles in a powder mass or compacting the particles by heating them to a temperature below the melting point of the main constituent at a predetermined and closely controlled time-temperature regime, including heating and cooling phases, in a protective atmosphere. The porosity of the sintered material is controlled by the amount of particle compacting in the mold or glue, the particle size, and the particle distribution. The sintered particles permit passage of a cooling fluid through the tip electrode, as described in more detail below. The final shape of the tip can be obtained with a variety of techniques including machining, grinding, etching, or molding.

In one embodiment, a sintering process involves providing ceramic, polyethylene or Teflon powder particles in a certain sieve fraction, e.g., in the range of from about 5 microns to about 250 microns. The particles are preferably in the range of from about 10 microns to about 100 microns. In a particularly preferred embodiment, at least two different sized particles can be provided. For example, particles in the range of from about 15 microns to about 30 microns, and more preferably about 20 microns, in combination with particles in the range of from about 80 microns to about 110 microns, and more preferably about 100 microns, could be used. When two different sized particles are used, preferably the larger particles have a mean diameter at least about 2.5 times greater than the mean diameter of the smaller particles, and more preferably at least about 4 times greater. Alternatively, a single particle size can be used, which can provide a denser packing and result in a higher pressure drop across the porous electrode. Whatever material is used, the particles are preferably rounded and more preferably spherical, so as to provide a tip electrode surface that is not rough. However, the particles can be irregularly shaped, i.e. having differing shapes, which is a low cost alternative. Tip surface irregularities could also be smoothed through secondary operations such as mechanical polishing and laser etching.

In one process, the particles are put into a mold, such as a ceramic mold, having the desired electrode shape. If desired, the particles can be mixed with a suitable binder prior to being put into the mold. When a binder is used, the mold containing the binder and particles is placed into a low temperature oven and heated to a temperature sufficient to evaporate the binder. The particles are then sintered under vacuum or air at a temperature ranging from about 80 degree C. to about 160 degree C., although the temperature can vary depending on the composition of the porous polymer. However, the temperature should be below the melting point of the composition. The resulting tip electrode is then removed from the mold and assembled onto the flexible tubing of the tip section.

Figure 6:
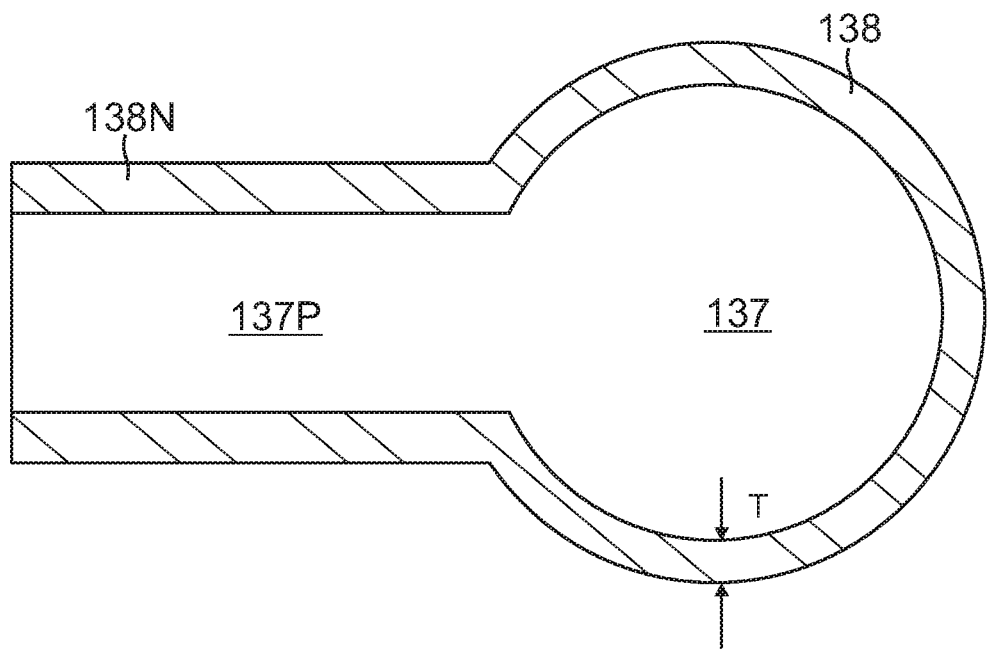
FIG. 6 is a side cross-sectional view of a porous substrate, in accordance with another embodiment.
Figure 7:
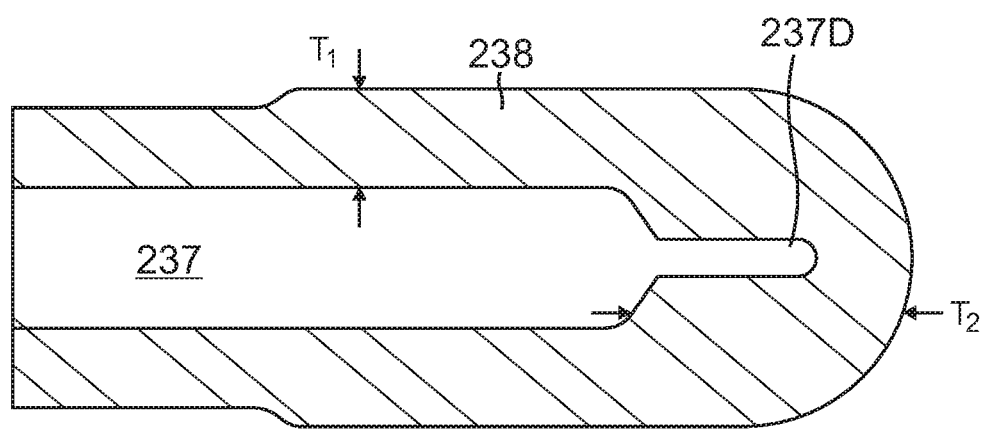
FIG. 7 is a side cross-sectional view of a porous substrate, in accordance with yet another embodiment.

In the embodiment of FIG. 4, the porous substrate 38 has a generally cylindrical shape with domed distal end. However, it is understood that the porous substrate may have different shapes, as desired or appropriate. For example, porous substrate 138 of FIG. 6 has a bulbous shape and an elongated stem portion 138N, along with a bulbous shaped chamber 137 with an elongated proximal portion 137P. The wall thickness T is generally uniform throughout the substrate 138. Moreover, it is understood that the porous substrate and the chamber may have dissimilar shapes. For example, substrate 238 of FIG. 7 is generally cylindrical with a domed distal end, but its chamber 237 is cylindrical with a narrowed distal end 237D which is adapted for receiving and anchoring a distal end of the electrifying lead wire. Likewise, the wall thickness may vary throughout the substrate, some portions T1 being thinner and other portions T2 being thicker.

Disposed over the surface of the porous substrate are the one or more sensing microelectrodes 40 in the form of individual and separate thin metal coatings, as depicted in FIGS. 5A-5D. It is understood that the thin metal coatings may be applied in close proximity to each other using any suitable process, including, for example, metallization, core plating, electroplating and/or 3-D printing, and may involve more than one layers, with the outer most layer comprising suitable electrode material (or alloys) known in the art, such as gold, platinum, platinum/iridium. In accordance with a feature of the present invention, the one or more metal coatings are made of conductive material that is also MRI-compatible, (e.g. platinum or gold). In some embodiments, the metal coating 40 is made of a platinum-iridium alloy, e.g. 90% Platinum/10% Iridium, applied to the surface of the porous substrate 38 by metallization treatment or process impregnating a thin layer of platinum-iridium alloy onto the porous substrate 38, as known in the art.

Figure 5A:
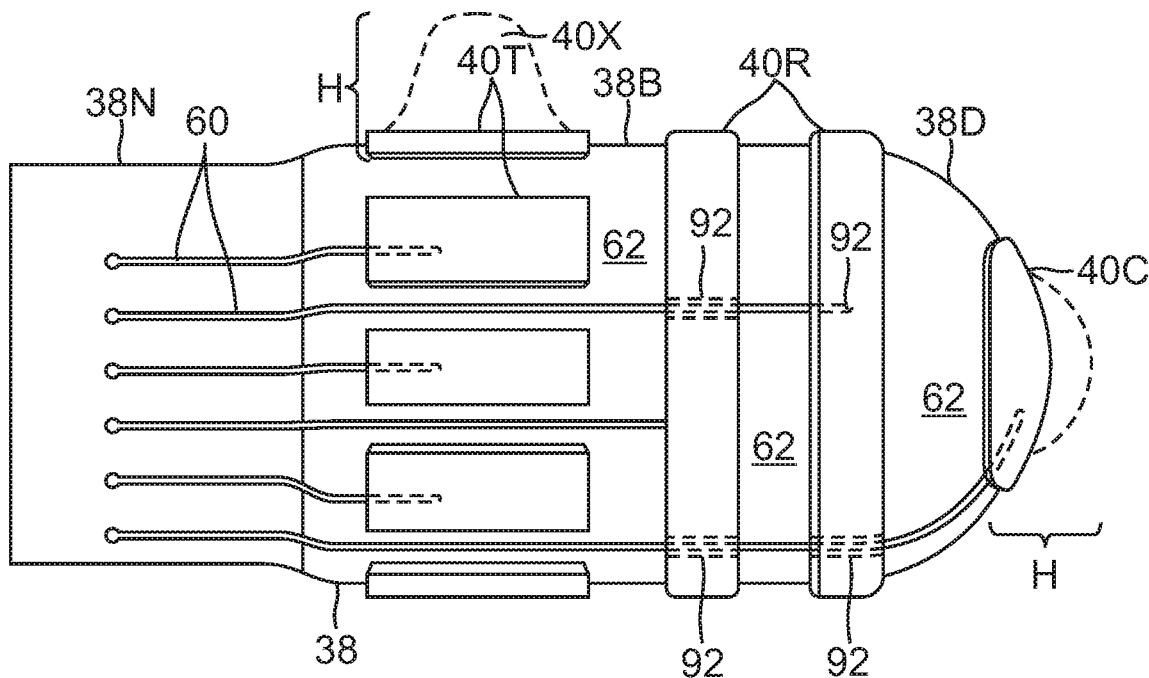
FIG. 5A is a side view of a tip electrode in accordance with a first embodiment.
Figure 5B:
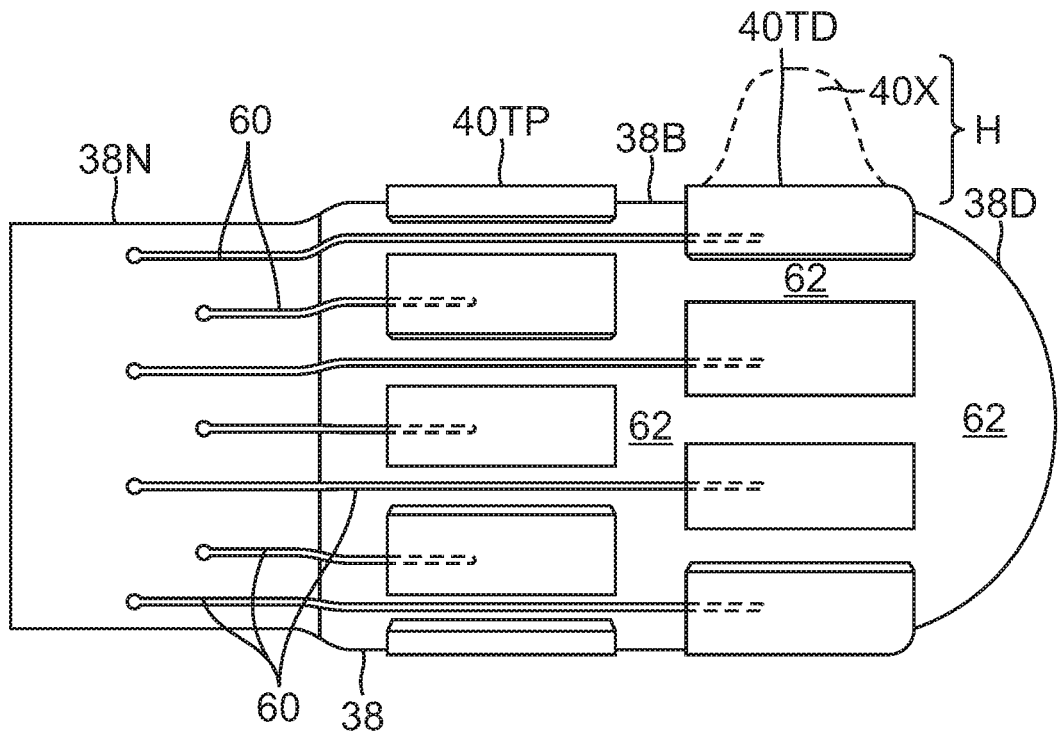
FIG. 5B is a side view of a tip electrode in accordance with a second embodiment.
Figure 5C:
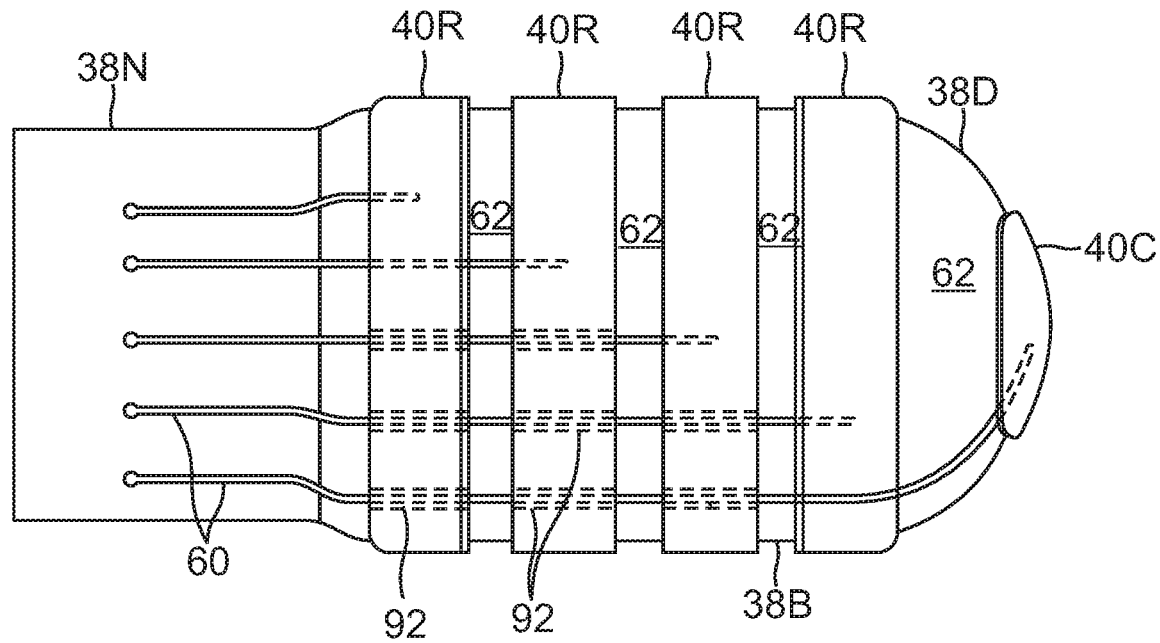
FIG. 5C is a side view of a tip electrode in accordance with a third embodiment.
Figure 5D:
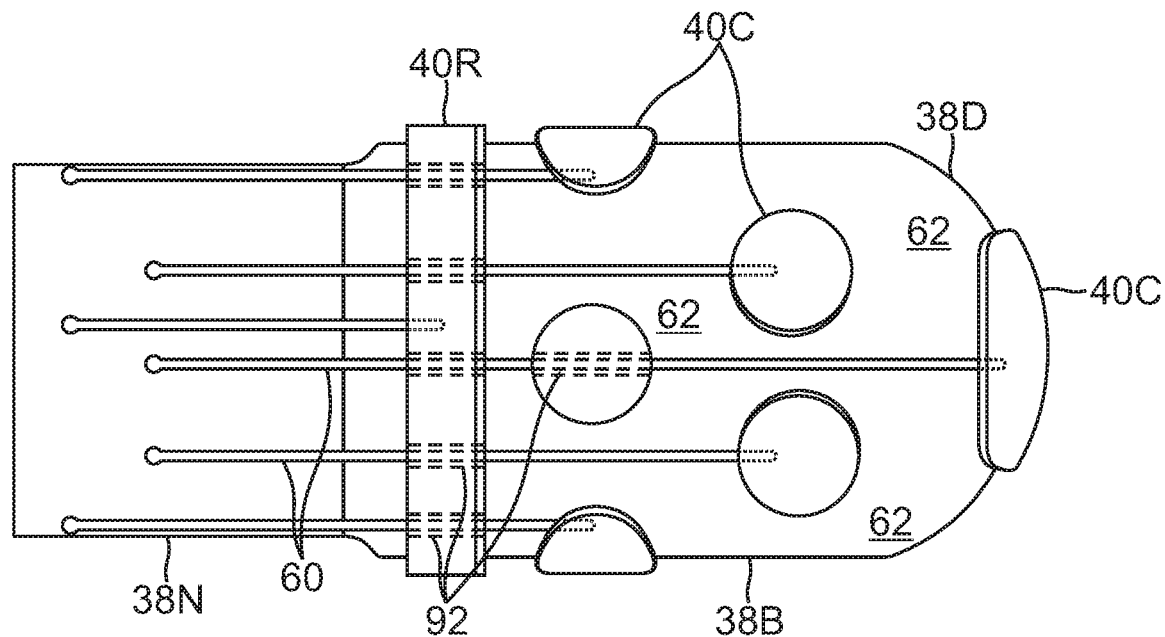
FIG. 5D is a side view of a tip electrode in accordance with a fourth embodiment.
Figure 5E:
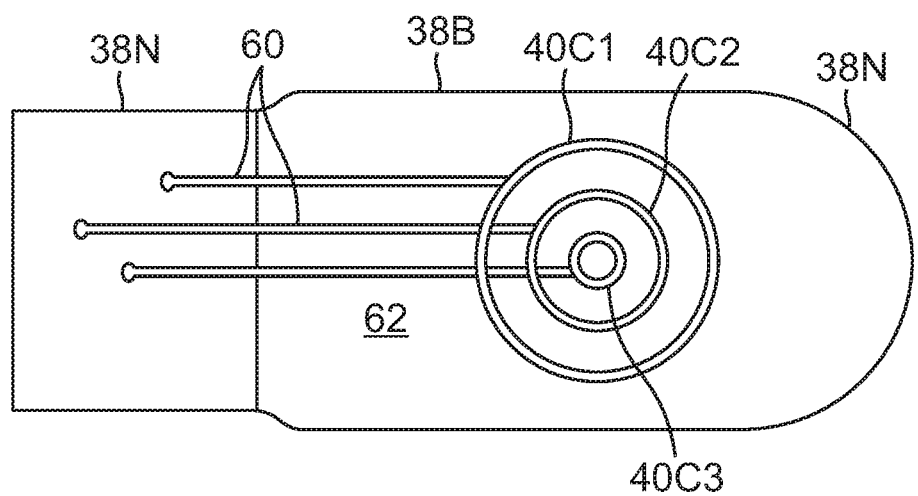
FIG. 5E is a side view of a tip electrode in accordance with a fifth embodiment.

The thickness of the metal coating may vary as desired. The thickness can be uniform or not uniform. For example, the metal coating may have a uniform thickness ranging from 0.2 μm to about 2.0 μm. In some embodiments, coating forming one or more microelectrodes 40X, as shown in FIGS. 5A and 5B, has non-uniform thickness e.g. thicker towards the center and thinner towards the periphery. This allows for a protrusion configuration or a raised profile. The ratio of the central thickness H to the thickness at the periphery may range between about 2 and 20. Such-protruding-shape allows for improved contact with the heart tissue and consequently improved electrogram quality.

As shown in FIGS. 5A-5E, the metal coatings can be of any desired plurality of any desired configuration and/or orientation to form individual and separate surface microelectrodes, for example, circular, oval, rectangular, elongated, ring, axial, radial, and co-centric. For example, in FIG. 5A, the metal coatings provide axial proximal rectangular surface micro-electrodes 40T, more distal ring surface micro-electrodes 40R, and distal tip circular surface micro-electrode 40C. For example, in FIG. 5B, the metal coatings provide axial proximal rectangular surface micro-electrodes 40TP and axial distal rectangular surface micro-electrodes 40TD that are axially offset from each other. For example, in FIG. 5C, the metal coatings provide a plurality (four) of rings surface micro-electrodes 40R and a distal tip circular surface micro-electrode 40C. For example, in FIG. 5D, the metal coatings provide a distal tip circular surface micro-electrode 40C, a plurality of smaller circular micro-electrodes 40C and a proximal ring surface micro-electrode 40R. For example, in FIG. 5E, a series of concentric circular surface micro-electrodes 40C1, 40C2 and 40C3 of different radii is shown on one side of the tip. It is understood that the size of the micro-surface electrodes in the drawings herein, including FIGS. 5A-5E, is not to scale and that their size is exaggerated so as to show their structure with better clarity.

Figure 3A:
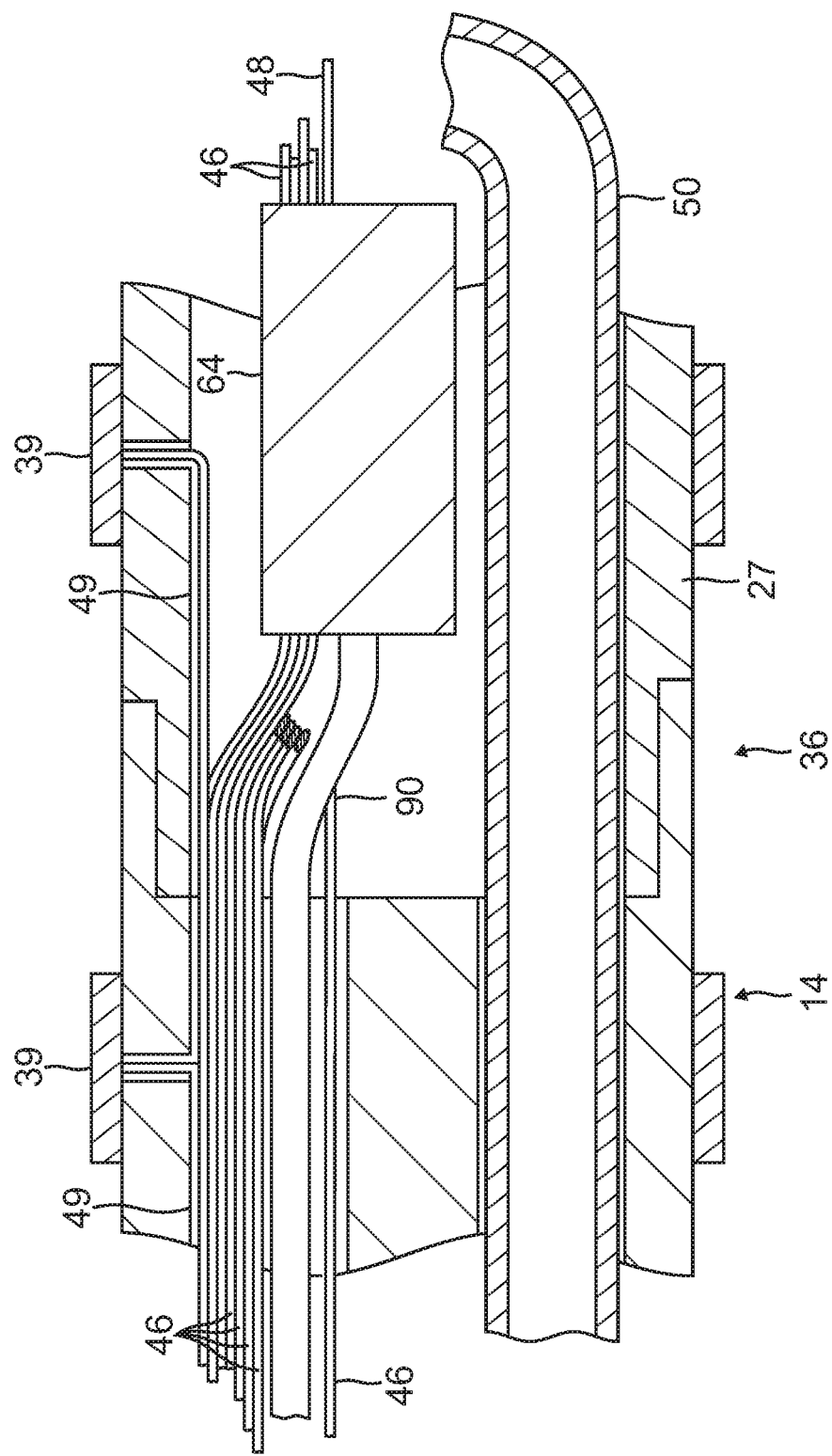
FIG. 3A is a side cross-sectional view of the catheter of FIG. 1, including a junction between the deflection section and a distal electrode section, taken along a first diameter.

Advantageously, the surface electrodes 40 are sized as micro-electrodes for obtaining highly localized electrograms and providing high density mapping of heart tissue. The surface area of each surface electrode ranges between about 0.2 mm$^2$ and 2.0 mm$^2$, preferably between about 0.5 mm$^2$ and 1 mm$^2$. In that regard, it is understood that the figures herein are not necessarily to scale. The plurality of surface electrodes on the substrate may range between about one and 20, preferably about two and 10. Each surface electrode 40 is connected to a respective lead wire 46 whose proximal end terminates in the control handle 16 in an input jack (not shown) that may be plugged into an appropriate signal processor (not shown). The lead wires 46 extend from the control handle 16 and through the central lumen 18 of the catheter body (FIG. 2A), the first lumen 30 of tubing 19 of the deflection section 14 (FIG. 2A), and the lumen of the connector tube 27 (FIG. 3A). The portion of the lead wires 46 extending through at least the catheter body 12 and the deflection section 14 may be enclosed within a protective sheath (not shown), which can be made of any suitable material, preferably polyimide. The protective sheath may be anchored at its distal end to the proximal end of the deflection section 14 by gluing it in the first lumen 30 with polyurethane glue or the like.

Figure 4B:
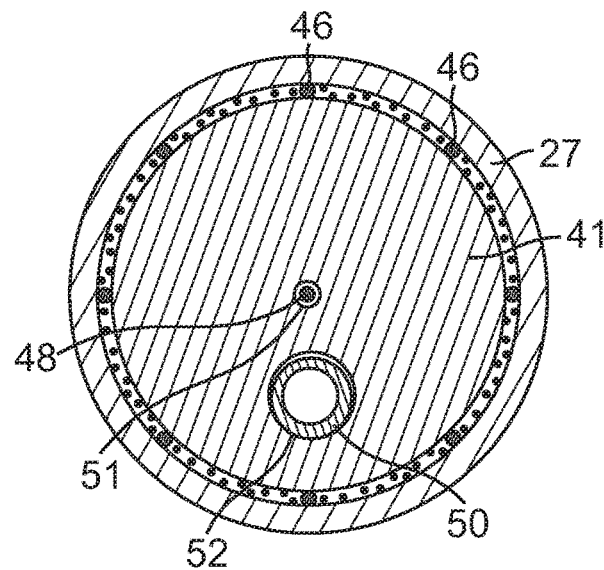
FIG. 4B is an end cross-sectional view of the distal electrode section of FIG. 4, taken along line B-B.

The lead wires 46 are attached or electrically connected to the surface electrodes 40 through surface electrode leads 60 (FIGS. 5A-5E) which may be applied or deposited on the outer surface of the porous substrate 38 and the stem portion 38N in the same manner as the surface microelectrodes 40, as described above. As shown in FIGS. 4 and 4B, distal end portions of lead wires 46 pass between an inner surface of the connector tubing 27 and the peripheral edge of the plug member 41 and the outer surface of the stem portion 38N. These surfaces at and near the proximal end of the substrate 38 may be sealed by glue and the like. Distal ends of the lead wires 46 are attached to respective proximal ends of the surface electrode leads 60 at or near the distal end of the connector tubing 27. Accordingly, electrical signals of the heart tissue sensed by the microelectrodes are transmitted proximally toward the control handle via the surface electrode leads 60 and the lead wires 46.

As understood by one of ordinary skill in the art, selected surface electrode leads 60 and surface sensing microelectrodes 40 are insulated from each other where they overlap each other. An insulating layer may be placed in between surface electrode leads 60 and surface electrodes 40 and grooves 92 (FIGS. 5A, 5C and 5E) may be formed on the outer surface of the porous substrate for underpassing surface electrode leads 60 so that overlying surface electrodes 40 can lie flat on the outer surface of the porous substrate 38.

For ablation purposes, the porous substrate 38 is "energized" by the lead wire 48 which passes into the chamber 37 via the first through-hole 51 in the plug member 41. When energized, the lead wire 48 renders the porous substrate 38 into a "virtual" ablation electrode by conducting the energy through the conductive-irrigation fluid, e.g., saline, delivered by the irrigation tubing 50 which enters the chamber 37 and weeps through the porous substrate 38 in providing a generally uniform thin layer of energized fluid throughout its exposed surfaces 62 (in between the surface microelectrodes 40) to further improve ablation safety. Wherever the fluid is present on or flowing from the porous substrate 38, ablation may be accomplished therefrom.

Figure 4C:
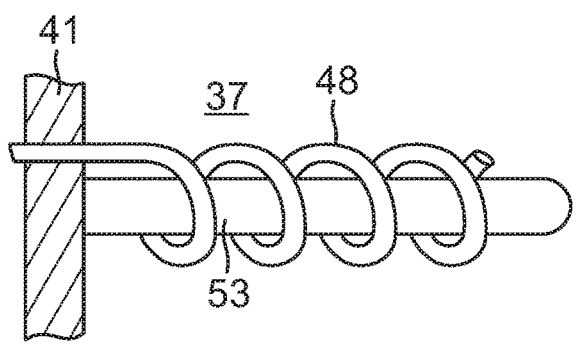
FIG. 4C is a side view of a distal portion of a lead wire in a chamber, in accordance with one embodiment.
Figure 4D:
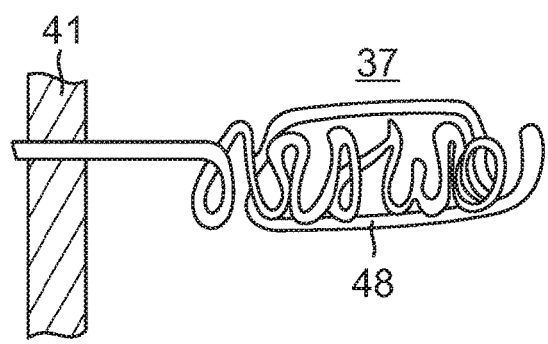
FIG. 4D is a side view of a distal portion of a lead wire in a chamber, in accordance with another embodiment.

In the embodiment of FIG. 4, the distal portion of the lead wire 48 in the chamber 37 is elongated and linear. However, it is understood that the distal portion may assume any shape as desired or appropriate. The distal portion of the lead wire 48 in the chamber 37 may be configured nonlinearly, for example, wrapped around itself (FIG. 4D) or coiled around a support member 53 (FIG. 4C) for increased surface area exposure and contact with the fluid in the chamber 37 for greater conduction between the lead wire and the fluid. A proximal end of the support member 53 may be affixed to and mounted on a distal face of the plug member.

Figure 4E:
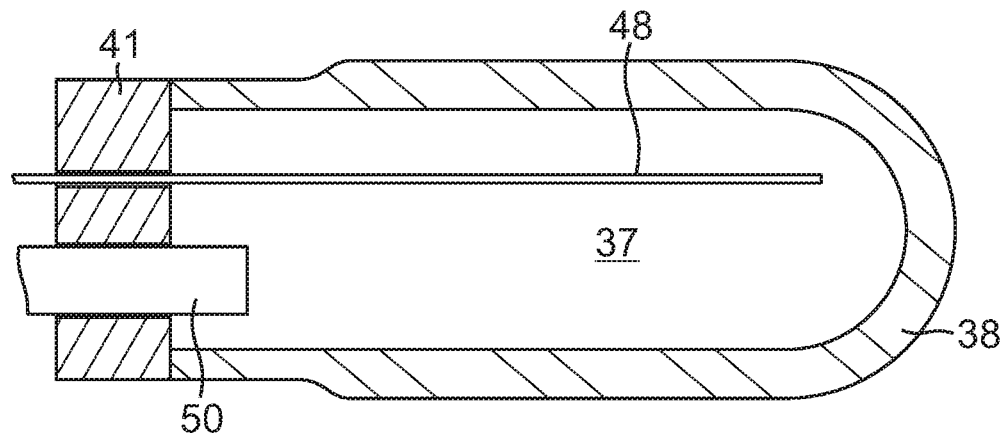
FIG. 4E is a side view of a distal portion of a lead wire in a chamber, in accordance with another embodiment.
Figure 4F:
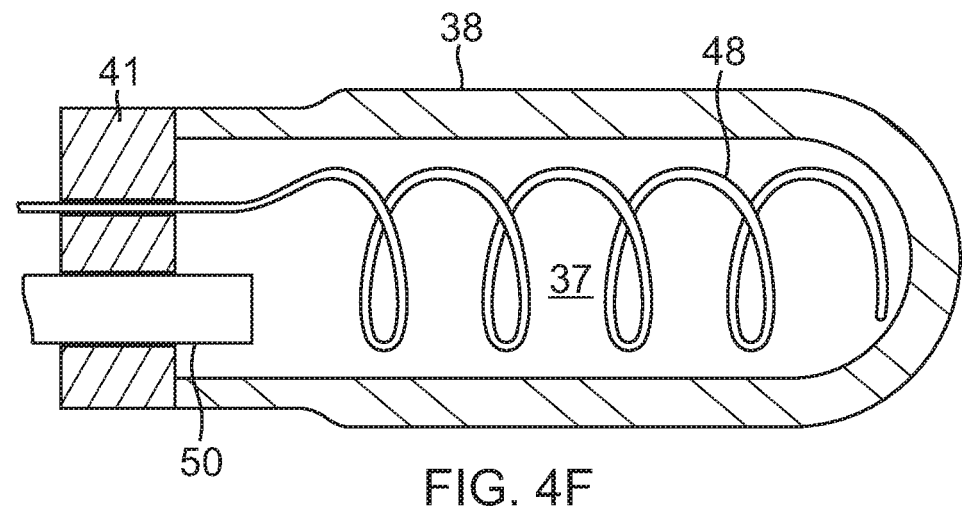
FIG. 4F is a side view of a distal portion of a lead wire in a chamber, in accordance with another embodiment.
Figure 4G:
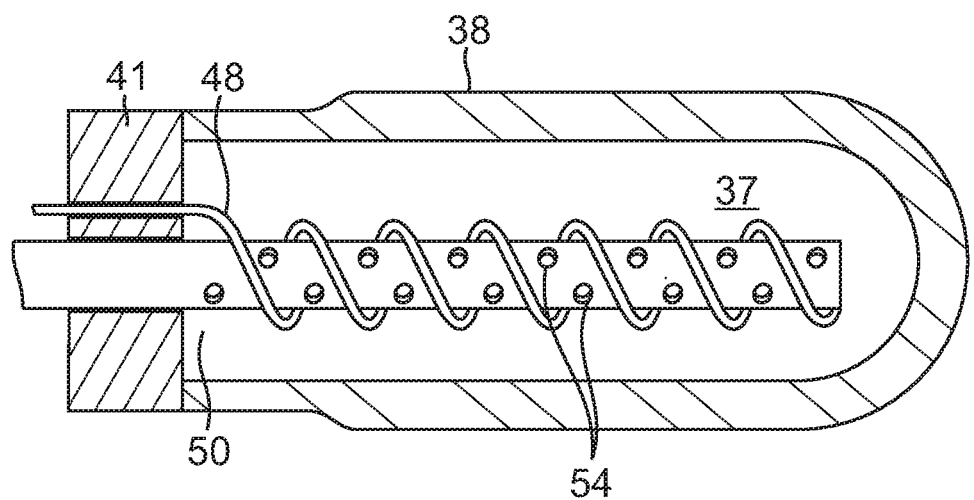
FIG. 4G is a side view of a distal portion of a lead wire and an irrigation tubing in a chamber, in accordance with another embodiment.

The distal portion of the lead wire 48 may also extend linearly and deeply distally in the chamber 37 along the longitudinal center axis (FIG. 4E), spiral widely approaching the inner surface of the chamber 37 (FIG. 4F), or be wrapped or coiled around an extended distal portion of the irrigation tubing 40 such that both extend deeply distally in the chamber 37. The irrigation tubing 40 may be perforated with pores 54 along its length (FIG. 4G). Such configuration improves the uniformity of irrigation within the chamber 37 and the tip 36 and allows for even greater exposure of the lead wire to the conductive fluid.

Figure 3B:
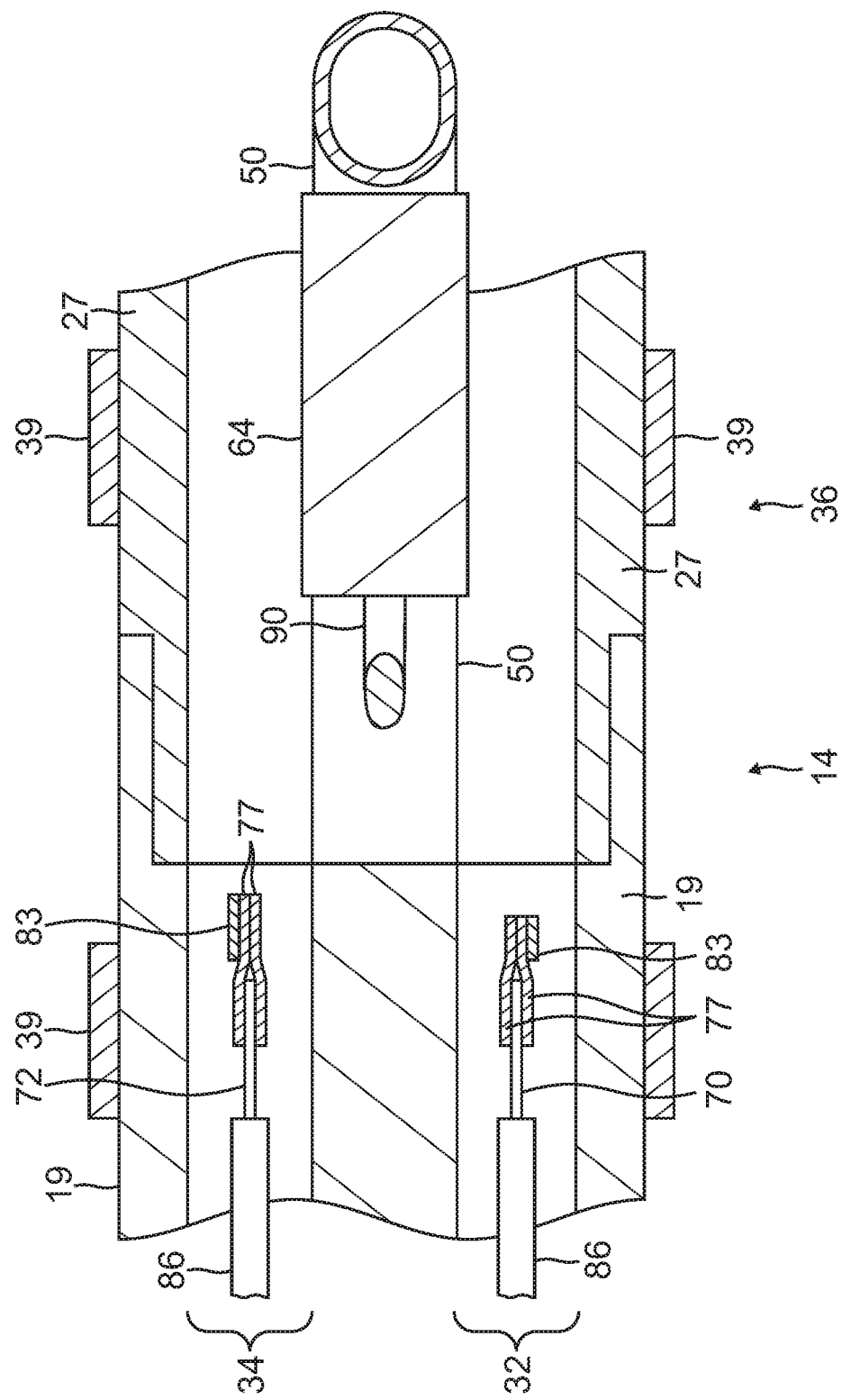
FIG. 3B is a side cross-sectional view of the junction of FIG. 3A, taken along a second diameter generally perpendicular to the first diameter.

In the illustrated embodiment, the catheter includes three ring electrodes 39 proximal of the distal tip section 15, mounted on the tubing 19 of the deflection section 14 and/or the connector tubing 27, as shown in FIGS. 3A, 3B and 4. It is understood that the presence and number of ring electrodes 39 may vary as desired, likewise their function as monopolar or bipolar electrodes for local electrogram sensing and/or location referencing in relation to the location sensor 64 housed in the connector tubing 27. Each ring electrode 39 is slid over the tubing 19 and/or 27 and fixed in place by glue or the like. The ring electrodes 39 can be made of any suitable material, and are preferably machined from platinum-iridium bar (90% platinum/10% iridium), gold, or gold alloys.

Connection of a lead wire 49 to a ring electrode 39 is preferably accomplished by first making a small hole through the tubing 19 and/or 27. Such a hole can be created, for example, by inserting a needle through the tubing and heating the needle sufficiently to form a permanent hole. A lead wire 49 is then drawn through the hole by using a microhook or the like. The ends of the lead wire 49 are then stripped of any coating and soldered or welded to the underside of the ring electrode 39, which is then slid into position over the hole and fixed in place with polyurethane glue or the like.

The irrigation tubing 50 is provided within the catheter body 12 for infusing fluids, e.g. saline, to electrify the porous substrate 38 of the tip electrode 36 and provide cooling during ablation. The irrigation tubing 50 may be made of any suitable material, and is preferably made of polyimide tubing. In one embodiment, the irrigation tubing has an outer diameter of from about 0.032 inches to about 0.036 inches and an inner diameter of from about 0.027 inches to about 0.032 inches.

The irrigation tubing 50 extends from the control handle 16 and through the central lumen 18 of the catheter body 12 (FIG. 2A), the lumen 35 of the tubing 19 of the deflection section 14 (FIG. 3A), and the connector tube 27 (FIG. 3A), and into the second through-hole 52 in the plug member 41 and the chamber 37 of the substrate 38 (FIG. 4). The proximal end of the irrigation tubing 50 extends through the control handle 16 to a fluid source and a pump (not shown). The fluid introduced through the catheter is preferably a biologically compatible fluid such as saline, or water. In addition to, or instead of, being used to cool the tip electrode, the infused fluid also forms a buffer layer to maintain biological materials, such as blood, at a distance from the tip electrode, thereby minimizing contact of the tip electrode with the biological material. This buffer layer reduces coagulation of biological materials and regulates the impedance or resistance to energy transfer of the tissue near the tip electrode during ablation. Saline or any other conductive fluid is preferred where the tip electrode is to function as an ablative electrode.

The rate of fluid flow through the catheter may be controlled by any suitable fluid infusion pump or by pressure. A suitable infusion pump is the COOLFLOW available from Biosense Webster, Inc. (Diamond Bar, Calif.). The rate of fluid flow through the catheter preferably ranges from about 0.5 ml/min to about 30 ml/min, more preferably from about 2 ml/min to about 17 ml/min. Preferably, the fluid is maintained at about room temperature.

It is understood that a temperature sensing means is provided for the tip electrode 36, as known in the art. Any conventional temperature sensing means, e.g., a thermocouple or thermistor, may be used. A suitable thermistor for use in the present invention is Model No. AB6N2-GC14KA143E/37C sold by Thermometrics (New Jersey). The temperature sensing means may also be used as a feedback system to adjust the RF power delivered to the tissue through the catheter to maintain a desired temperature at the tip electrode.

As shown in FIGS. 2B and 3B, a pair of puller wires 70 and 72 extend through the catheter body 12 for bidirectional deflection. The puller wires 70 and 72 are anchored at their proximal end to the control handle 16, and are anchored at their distal ends to the deflection section 14 at or near its the distal end. The puller wires are made of any suitable metal, such as stainless steel or Nitinol, and may be coated with Teflon or the like. The coating imparts lubricity to the puller wires. Each of the puller wires may have a diameter ranging from about 0.006 inches to about 0.010 inches.

A compression coil 74 is situated within the catheter body 12 in surrounding relation to each puller wire 50 (FIG. 2B). Each compression coil 74 extends from the proximal end of the catheter body 12 to about the proximal end of the deflection section 14. The compression coils are made of any suitable metal, preferably stainless steel. Each compression coil 52 is tightly wound on itself to provide flexibility, i.e., bending, but to resist compression. The inner diameter of the compression coil is slightly larger than the diameter of the puller wire. The Teflon coating on the puller wires 70 and 72 allows them to slide freely within their respective compression coil. If desired, particularly if the lead wires 48 and 49 are not enclosed by a protective sheath, the outer surface of each compression coil can be covered by a flexible, non-conductive sheath 76, e.g., made of polyimide tubing, to prevent contact between the compression coil and any other wires within the catheter body 12.

Each compression coil 74 is anchored at its proximal end to the proximal end of the stiffening tube 20 in the catheter body 12 by a glue joint (not shown) and at its distal end to the deflection section 14 by glue joint 73 (FIG. 2B). Both glue joints may comprise polyurethane glue or the like. The glue may be applied by means of a needle or the like through a hole made in the side wall of the respective tubing, which needle is heated sufficiently to form a permanent hole. The glue is then introduced through the hole and wicks around the outer circumference to form a glue joint about the entire circumference of the compression coil.

The puller wires 70 and 72 extend into the lumens 32 and 34 (FIG. 2C), respectively, of the deflection section 14. The puller wires are anchored at their distal end to the deflection section 14. In one embodiment, an anchor is fixedly attached to the distal end of each puller wire, as depicted in FIG. 3B. The anchor is preferably formed by a metal tube 77, e.g. a short segment of hypodermic stock, which is fixedly attached, e.g. by crimping, to the distal end of the puller wires 70 and 72. The tubes 77 have a section that extends a short distance beyond the distal end of the puller wires. A cross-piece 83 made of a small section of stainless steel ribbon or the like is soldered or welded in a transverse arrangement to the distal end of each tube section 77, which is flattened during the operation. This creates a T-bar anchor. Two notches are created in the sidewall of the deflection section 14, resulting in openings into the lumens 32 and 34 into which the puller wires 70 and 72 extend. The anchors lie partially within the notches. Because the length of the ribbons forming the cross-pieces 83 are longer than the diameter of the openings into the lumens 32 and 34, the anchors cannot be pulled completely into the lumens 32 and 34. The notches are then sealed with polyurethane glue or the like to give a smooth outer surface. Within the lumens 32 and 34 of the deflection section 14, each of the puller wires 70 and 72 extends through a respective plastic, preferably Teflon sheath 86, which prevents the puller wires from cutting into the wall of the tubing 19 when the deflection section 14 is deflected.

Longitudinal movement of the puller wires 70 and 72 relative to the catheter body 12, which results in deflection of the deflection section 14, is accomplished by suitable manipulation of the control handle 16. A suitable control handle for use with the present invention is described in U.S. Pat. No. 6,120,476, the disclosure of which is incorporated herein by reference.

In the illustrated embodiment, an electromagnetic sensor 64 is provided and housed in the lumen of the connector tube 27. A sensor cable 90 extends from the control handle 16, and through the central lumen 18 of the catheter body 12 and the lumen 30 of the tubing 19 of deflection section 14 and the lumen of the connector tube 27. The sensor cable 90 extends out the proximal end of the control handle 16 within an umbilical cord (not shown) to a sensor control module (not shown) that houses a circuit board (not shown). Alternatively, the circuit board can be housed within the control handle 16, for example, as described in U.S. Pat. No. 5,964,757, the disclosure of which is incorporated herein by reference. The electromagnetic sensor cable 90 comprises multiple wires encased within a plastic covered sheath. In the sensor control module, the wires of the electromagnetic sensor cable are connected to the circuit board. The circuit board amplifies the signal received from the electromagnetic sensor and transmits it to a computer in a form understandable by the computer by means of the sensor connector at the proximal end of the sensor control module. Also, because the catheter is designed for single use only, the circuit board preferably contains an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443,489, 5,546,951, 5,568,809 and 5,391,199 and International Publication No. WO 95/02995, the disclosures of which are incorporated herein by reference. A preferred electromagnetic sensor 64 has a length of from about 6 mm to about 7 mm and a diameter of about 1.3 mm.

In use, a suitable guiding sheath (not shown) is inserted into the patient with its distal end positioned at or near a desired tissue location for diagnostics such as mapping and/or treatment such as ablation. An example of a suitable guiding sheath for use in connection with the present invention is the Preface Braided Guiding Sheath, commercially available from Biosense Webster, Inc. (Diamond Bar, Calif.). The catheter 10 is passed through the guiding sheath and advanced therethrough to the desired tissue location. The guiding sheath is pulled proximally, exposing the tip electrode section 15 and the deflection section 14.

The user actuates a thumb knob on the control handle to deflect the catheter and position the tip electrode 36 on tissue surface. With the multiple surface microelectrodes 40 in contact (or close proximity) with tissue, the catheter 10 is adapted for high density electrode sensing detecting electrical activity in the tissue which is transmitted through the catheter via the lead wires 46 for processing by a signal processor (not shown) for generating high density mapping with highly localized electrograms. If ablation is desired, the lead wire 48 is energized by an energy source, e.g., RF generator (not shown), whose distal end portion in the chamber 37 of the porous substrate 38 electrifies the conductive irrigation fluid delivered into the chamber 37 via irrigation tubing 50. Passing of such electrified fluid from the chamber to the exposed surfaces of the porous substrate 38 renders the porous substrate 38 into a "virtual" ablation electrode. During and after ablation, the surface microelectrodes 40 on the porous substrate 38 can sense electrical activity at and around the ablated tissue to confirm the formation of electrically blocked tissue regions.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of more or more embodiment may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
an elongated catheter body;
a distal electrode member distal of the catheter body and
having a porous substrate and a plurality of surface electrodes on portions of an outer surface of the porous substrate, the porous substrate having an interior chamber adapted to receive conductive fluid;

a plurality of lead traces on the outer surface of the porous substrate, each of the plurality of lead traces connected to a respective one of the plurality of surface electrodes, at least one of the plurality of lead traces having a portion extending underneath at least one other of the plurality of surface electrodes; and a chamber lead wire having a distal portion extending into the interior chamber, the chamber lead wire adapted to electrify the conductive fluid in the interior chamber, and the chamber lead wire having:
- a linear configuration extending generally along a longitudinal center axis of the interior chamber, or
- a linear configuration extending generally off-axis from the longitudinal center axis of the interior chamber, or
- a nonlinear configuration, the porous substrate being configured to pass the conductive fluid from the interior chamber to the outer surface of the porous substrate.

2. The catheter of claim 1, further comprising at least one insulating layer between the at least one other of the plurality of surface electrodes and the portion of the at least one of the plurality of lead traces extending underneath the at least one other of the plurality of surface electrodes.

3. The catheter of claim 1, wherein the porous substrate comprises an MRI-compatible material.

4. The catheter of claim 1, wherein the surface electrodes comprise an MRI-compatible material.

5. The catheter of claim 1, wherein the nonlinear configuration of the chamber lead wire comprises the chamber lead wire wrapped around itself.

6. The catheter of claim 1, wherein the nonlinear configuration of the chamber lead wire comprises the chamber lead wire coiled around a support member.

7. The catheter of claim 1, wherein the nonlinear configuration of the chamber lead wire comprises the chamber lead wire coiled within the interior chamber.

8. The catheter of claim 1, further comprising an irrigation tubing in fluid communication with the interior chamber and having a distal portion extending into the interior chamber.

9. The catheter of claim 8, wherein the chamber lead wire has the linear configuration in which the chamber lead wire extends generally off-axis from the longitudinal center axis of the interior chamber, and the distal portion of the irrigation tubing extends generally off-axis from the longitudinal center axis of the interior chamber.

10. The catheter of claim 8, wherein the nonlinear configuration of the chamber lead wire comprises the chamber lead wire coiled around the distal portion of the irrigation tubing.

11. The catheter of claim 8, wherein the distal portion of the irrigation tubing is perforated along its length.

12. A catheter comprising:
an elongated catheter body;
a distal electrode member distal of the catheter body and comprising:
- a porous substrate having an interior chamber adapted to receive conductive fluid,
- a plurality of distal surface electrodes arranged on an outer surface of the porous substrate, and
- a plurality of proximal surface electrodes arranged on the porous substrate proximal of the plurality of distal surface electrodes, the plurality of proximal surface electrodes being axially offset from the plurality of distal surface electrodes;
- a plurality of proximal lead traces, each of the plurality of proximal lead traces being connected to a respective one of the plurality of proximal surface electrodes;
- a plurality of distal lead traces, each of the plurality of distal lead traces being connected to a respective one of the plurality of distal surface electrodes, at least one of the plurality of distal lead traces having a portion extending between two adjacent ones of the plurality of proximal surface electrodes; and
- a lead wire having a distal portion extending into the interior chamber, the lead wire configured to electrify the conductive fluid in the chamber, and the lead wire having:
  - a linear configuration extending generally along a longitudinal center axis of the interior chamber, or
  - a linear configuration extending generally off-axis from the longitudinal center axis of the interior chamber, or a nonlinear configuration,
wherein the porous substrate is configured to pass the conductive fluid from the chamber to the outer surface of the porous substrate.

13. The catheter of claim 12, wherein the porous substrate, the plurality of distal surface electrodes, and the plurality of proximal surface electrodes each independently comprises an MRI-compatible material.

14. The catheter of claim 12, wherein the nonlinear configuration of the chamber lead wire comprises the chamber lead wire wrapped around itself.

15. The catheter of claim 12, wherein the nonlinear configuration of the chamber lead wire comprises the chamber lead wire coiled around a support member.

16. The catheter of claim 12, wherein the nonlinear configuration of the chamber lead wire comprises the chamber lead wire coiled within the interior chamber.

17. The catheter of claim 12, further comprising an irrigation tubing in fluid communication with the interior chamber and having a distal portion extending into the interior chamber.

18. The catheter of claim 17, wherein the chamber lead wire has the linear configuration in which the chamber lead wire extends generally off-axis from the longitudinal center axis of the interior chamber, and the distal portion of the irrigation tubing extends generally off-axis from the longitudinal center axis of the interior chamber.

19. The catheter of claim 17, wherein the nonlinear configuration of the chamber lead wire comprises the chamber lead wire coiled around the distal portion of the irrigation tubing.

20. The catheter of claim 17, wherein the distal portion of the irrigation tubing is perforated along its length.

* * * * *